US009457058B2

(12) United States Patent
Hondmann et al.

(10) Patent No.: US 9,457,058 B2
(45) Date of Patent: *Oct. 4, 2016

(54) NUTRITIONAL COMPOSITION CONTAINING A PEPTIDE COMPONENT WITH ANTI-INFLAMMATORY PROPERTIES AND USES THEREOF

(71) Applicant: Mead Johnson Nutrition Company, Glenview, IL (US)

(72) Inventors: Dirk Hondmann, Winnetka, IL (US); Eric A. F. van Tol, Arnhem (NL); Gabriele Gross, Nijmegen (NL); Marieke H. Schoemaker, Rhenen (NL); Teartse Tim Lambers, Nijmegen (NL)

(73) Assignee: Mead Johnson Nutrition Company, Glenview, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/513,584

(22) Filed: Oct. 14, 2014

(65) Prior Publication Data

US 2015/0093463 A1 Apr. 2, 2015

Related U.S. Application Data

(62) Division of application No. 13/833,094, filed on Mar. 15, 2013, now Pat. No. 8,889,633.

(51) Int. Cl.

| | | |
|---|---|---|
| *A23L 1/305* | (2006.01) | |
| *A61K 38/08* | (2006.01) | |
| *A61K 31/202* | (2006.01) | |
| *A61K 31/70* | (2006.01) | |
| *A61K 35/741* | (2015.01) | |
| *A61K 38/07* | (2006.01) | |
| *A61K 38/01* | (2006.01) | |
| *A23L 1/30* | (2006.01) | |
| *A23L 1/29* | (2006.01) | |
| *A61K 38/06* | (2006.01) | |
| *A61K 45/06* | (2006.01) | |

(52) U.S. Cl.
CPC .............. *A61K 38/08* (2013.01); *A23L 1/296* (2013.01); *A23L 1/3014* (2013.01); *A23L 1/3053* (2013.01); *A61K 31/202* (2013.01); *A61K 31/70* (2013.01); *A61K 35/741* (2013.01); *A61K 38/018* (2013.01); *A61K 38/06* (2013.01); *A61K 38/07* (2013.01); *A61K 45/06* (2013.01); *A23V 2002/00* (2013.01)

(58) Field of Classification Search
CPC .................... A23L 1/296; A23C 9/1526
See application file for complete search history.

(56) References Cited

U.S. PATENT DOCUMENTS

| | | | |
|---|---|---|---|
| 5,405,637 A | 4/1995 | Martinez et al. | |
| 6,180,761 B1 | 1/2001 | Han et al. | |
| 6,495,344 B1 | 12/2002 | Carr et al. | |
| 7,091,320 B2 | 8/2006 | Pozzilli et al. | |
| 7,550,436 B2 | 6/2009 | Takahashi et al. | |
| 7,579,315 B2 | 8/2009 | Smith et al. | |
| 7,618,669 B2 * | 11/2009 | Rangavajla | A23J 3/34 426/43 |
| 7,629,744 B2 | 12/2009 | Ahn et al. | |
| 8,859,210 B2 | 10/2014 | Valenta et al. | |
| 2002/0147144 A1 | 10/2002 | Sidelman | |
| 2004/0180380 A1 | 9/2004 | Lee et al. | |
| 2007/0203060 A1 | 8/2007 | Sidelman et al. | |
| 2008/0096794 A1 | 4/2008 | Boehman et al. | |
| 2009/0036351 A1 | 2/2009 | Boots | |
| 2011/0177044 A1 | 7/2011 | Thomas et al. | |

FOREIGN PATENT DOCUMENTS

| | | |
|---|---|---|
| EP | 2017283 | 1/2009 |
| EP | 2332428 | 6/2011 |
| WO | 9111918 | 8/1991 |
| WO | 9212711 | 8/1992 |
| WO | 0137850 | 5/2001 |
| WO | 0219832 | 3/2002 |
| WO | 2005027953 | 3/2005 |
| WO | 2005117933 | 12/2005 |
| WO | 2006068480 | 6/2006 |
| WO | 2007060421 | 5/2007 |
| WO | 2007064208 | 6/2007 |
| WO | 2008004794 | 1/2008 |
| WO | 2008054192 | 5/2008 |

(Continued)

OTHER PUBLICATIONS

Appendices 1-3, locations of the peptides of Table 1 in full-length casein proteins of bovine milk, Feb. 2, 2016.*
GenBank Record No. ABW98936.1, alpha S1-casein, Bos taurus, 1989.*
GenBank Record No. AAA30431.1, beta casein, Bos taurus, 1993.*
GenBank Record No. AAQ87922.1, kappa casein, Bos taurus, 2005.*
Brugman, S., et al., "Neonatal oral administration of DiaPep277, combined with hydrolyzed casein diet, protects against Type 1 diabetes in BB-DP rats. An experimental study," Diabetologia, vo. 47, No. 7, Jan. 1, 2004.

(Continued)

*Primary Examiner* — Rosanne Kosson
(74) *Attorney, Agent, or Firm* — Patterson Intellectual Property Law, P.C.; James R. Cartiglia; Bethany J. Whelan

(57) ABSTRACT

The present disclosure relates to nutritional compositions comprising a protein equivalent source, wherein 20% to 80% of the protein equivalent source includes a peptide component comprising SEQ ID NO 4, SEQ ID NO 13, SEQ ID NO 17, SEQ ID NO 21, SEQ ID NO 24, SEQ ID NO 30, SEQ ID NO 31, SEQ ID NO 32, SEQ ID NO 51, SEQ ID NO 57, SEQ ID NO 60, and SEQ ID NO 63, and 20% to 80% of the protein equivalent source comprises an intact protein, a partially hydrolyzed protein, or combinations thereof. The disclosure further relates to methods of reducing the inflammatory response and/or production of proinflammatory cytokines, i.e. Interleukin-17, by providing said nutritional compositions to a target subject.

16 Claims, No Drawings

(56) References Cited

FOREIGN PATENT DOCUMENTS

| WO | 2008153429 | 5/2009 |
|---|---|---|
| WO | 2010043724 | 4/2010 |
| WO | 2010125192 | 11/2010 |

OTHER PUBLICATIONS

Mao, X.Y., et al., "Free-radical-scavenging and anti-inflammatory effect of yak milk casein before and after enzymatic hydrolysis," Food Chemistry, vol. 126, No. 2, May 15, 2011.
Nakamura, Y., et al., "Metabolic diseases and pro- and prebiotics: Mechanistic insights," Nutrition & Metabolism 2012, 9:60.
Peptide Protein Calculator, http://www.basic.northwestern.edu/biotools/proteincalc.html; downloaded on Nov. 18, 2014.
Visser, J., et al., "Potential mechanisms explaining why hydrolyzed casein-based diets outclass single amino acid-based diets in the prevention of autoimmune diabetes in diabetes-prone BB rats," Diabetes Metab Res Rev 2012;28:505-513.
Visser, J., et al., "Restoration of impaired intestinal barrier function by hydrolysed casein diet contributes to the prevention of type 1 diabetes in the diabetes-prone BioBreeding rat," Diabetologia (2010) 53:2621-2628.
Wielinga, P., et al., "Arachidonic acid/docosahexaenoic acid-supplemented diet in early life reduces body weight gain, plasma lipids, and adiposity in later life in ApoE*3Leiden mice," Mol. Nutr. Food Res. 2012, 56, 1081-1089.

* cited by examiner

SEQUENCE LISTING

```
<160> NUMBER OF SEQ ID NOS: 64

<210> SEQ ID NO 1
<211> LENGTH: 8
<212> TYPE: PRT
<213> ORGANISM: Bovine

<400> SEQUENCE: 1

Ala Ile Asn Pro Ser Lys Glu Asn
1               5

<210> SEQ ID NO 2
<211> LENGTH: 5
<212> TYPE: PRT
<213> ORGANISM: BOVINE
```

<400> SEQUENCE: 2

Ala Pro Phe Pro Glu
1               5

<210> SEQ ID NO 3
<211> LENGTH: 6
<212> TYPE: PRT
<213> ORGANISM: BOVINE

<400> SEQUENCE: 3

Asp Ile Gly Ser Glu Ser
1               5

<210> SEQ ID NO 4
<211> LENGTH: 7
<212> TYPE: PRT
<213> ORGANISM: BOVINE

<400> SEQUENCE: 4

Asp Lys Thr Glu Ile Pro Thr
1               5

<210> SEQ ID NO 5
<211> LENGTH: 5
<212> TYPE: PRT
<213> ORGANISM: BOVINE

<400> SEQUENCE: 5

Asp Met Glu Ser Thr
1               5

<210> SEQ ID NO 6
<211> LENGTH: 4
<212> TYPE: PRT
<213> ORGANISM: BOVINE

<400> SEQUENCE: 6

Asp Met Pro Ile
1

<210> SEQ ID NO 7
<211> LENGTH: 4
<212> TYPE: PRT
<213> ORGANISM: BOVINE

<400> SEQUENCE: 7

Asp Val Pro Ser
1

<210> SEQ ID NO 8
<211> LENGTH: 7
<212> TYPE: PRT
<213> ORGANISM: BOVINE

<400> SEQUENCE: 8

Glu Thr Ala Pro Val Pro Leu
1               5

<210> SEQ ID NO 9
<211> LENGTH: 6
<212> TYPE: PRT
<213> ORGANISM: BOVINE

<400> SEQUENCE: 9

Phe Pro Gly Pro Ile Pro
1               5

<210> SEQ ID NO 10
<211> LENGTH: 7
<212> TYPE: PRT
<213> ORGANISM: BOVINE

<400> SEQUENCE: 10

Phe Pro Gly Pro Ile Pro Asn
1               5

<210> SEQ ID NO 11
<211> LENGTH: 4
<212> TYPE: PRT
<213> ORGANISM: BOVINE

<400> SEQUENCE: 11

Gly Pro Phe Pro
1

<210> SEQ ID NO 12
<211> LENGTH: 4
<212> TYPE: PRT
<213> ORGANISM: BOVINE

<400> SEQUENCE: 12

Gly Pro Ile Val
1

<210> SEQ ID NO 13
<211> LENGTH: 9
<212> TYPE: PRT
<213> ORGANISM: BOVINE

<400> SEQUENCE: 13

Ile Gly Ser Glu Ser Thr Glu Asp Gln
1               5

<210> SEQ ID NO 14
<211> LENGTH: 8
<212> TYPE: PRT
<213> ORGANISM: BOVINE

<400> SEQUENCE: 14

Ile Gly Ser Ser Ser Glu Glu Ser
1               5

<210> SEQ ID NO 15
<211> LENGTH: 9
<212> TYPE: PRT
<213> ORGANISM: BOVINE

<400> SEQUENCE: 15

Ile Gly Ser Ser Ser Glu Glu Ser Ala
1               5

<210> SEQ ID NO 16
<211> LENGTH: 6
<212> TYPE: PRT
<213> ORGANISM: BOVINE

<400> SEQUENCE: 16

Ile Asn Pro Ser Lys Glu

```
1               5

<210> SEQ ID NO 17
<211> LENGTH: 5
<212> TYPE: PRT
<213> ORGANISM: BOVINE

<400> SEQUENCE: 17

Ile Pro Asn Pro Ile
1               5

<210> SEQ ID NO 18
<211> LENGTH: 6
<212> TYPE: PRT
<213> ORGANISM: BOVINE

<400> SEQUENCE: 18

Ile Pro Asn Pro Ile Gly
1               5

<210> SEQ ID NO 19
<211> LENGTH: 9
<212> TYPE: PRT
<213> ORGANISM: BOVINE

<400> SEQUENCE: 19

Ile Pro Pro Leu Thr Gln Thr Pro Val
1               5

<210> SEQ ID NO 20
<211> LENGTH: 4
<212> TYPE: PRT
<213> ORGANISM: BOVINE

<400> SEQUENCE: 20

Ile Thr Ala Pro
1

<210> SEQ ID NO 21
<211> LENGTH: 4
<212> TYPE: PRT
<213> ORGANISM: BOVINE

<400> SEQUENCE: 21

Ile Val Pro Asn
1

<210> SEQ ID NO 22
<211> LENGTH: 7
<212> TYPE: PRT
<213> ORGANISM: BOVINE

<400> SEQUENCE: 22

Lys His Gln Gly Leu Pro Gln
1               5

<210> SEQ ID NO 23
<211> LENGTH: 5
<212> TYPE: PRT
<213> ORGANISM: BOVINE

<400> SEQUENCE: 23

Leu Asp Val Thr Pro
1               5
```

```
<210> SEQ ID NO 24
<211> LENGTH: 6
<212> TYPE: PRT
<213> ORGANISM: BOVINE

<400> SEQUENCE: 24

Leu Glu Asp Ser Pro Glu
1               5

<210> SEQ ID NO 25
<211> LENGTH: 5
<212> TYPE: PRT
<213> ORGANISM: BOVINE

<400> SEQUENCE: 25

Leu Pro Leu Pro Leu
1               5

<210> SEQ ID NO 26
<211> LENGTH: 6
<212> TYPE: PRT
<213> ORGANISM: BOVINE

<400> SEQUENCE: 26

Met Glu Ser Thr Glu Val
1               5

<210> SEQ ID NO 27
<211> LENGTH: 11
<212> TYPE: PRT
<213> ORGANISM: BOVINE

<400> SEQUENCE: 27

Met His Gln Pro His Gln Pro Leu Pro Pro Thr
1               5                   10

<210> SEQ ID NO 28
<211> LENGTH: 5
<212> TYPE: PRT
<213> ORGANISM: BOVINE

<400> SEQUENCE: 28

Asn Ala Val Pro Ile
1               5

<210> SEQ ID NO 29
<211> LENGTH: 5
<212> TYPE: PRT
<213> ORGANISM: BOVINE

<400> SEQUENCE: 29

Asn Glu Val Glu Ala
1               5

<210> SEQ ID NO 30
<211> LENGTH: 6
<212> TYPE: PRT
<213> ORGANISM: BOVINE

<400> SEQUENCE: 30

Asn Gln Glu Gln Pro Ile
1               5

<210> SEQ ID NO 31
```

```
<211> LENGTH: 5
<212> TYPE: PRT
<213> ORGANISM: BOVINE

<400> SEQUENCE: 31

Asn Val Pro Gly Glu
1               5

<210> SEQ ID NO 32
<211> LENGTH: 6
<212> TYPE: PRT
<213> ORGANISM: BOVINE

<400> SEQUENCE: 32

Pro Phe Pro Gly Pro Ile
1               5

<210> SEQ ID NO 33
<211> LENGTH: 6
<212> TYPE: PRT
<213> ORGANISM: BOVINE

<400> SEQUENCE: 33

Pro Gly Pro Ile Pro Asn
1               5

<210> SEQ ID NO 34
<211> LENGTH: 8
<212> TYPE: PRT
<213> ORGANISM: BOVINE

<400> SEQUENCE: 34

Pro His Gln Pro Leu Pro Pro Thr
1               5

<210> SEQ ID NO 35
<211> LENGTH: 5
<212> TYPE: PRT
<213> ORGANISM: BOVINE

<400> SEQUENCE: 35

Pro Ile Thr Pro Thr
1               5

<210> SEQ ID NO 36
<211> LENGTH: 4
<212> TYPE: PRT
<213> ORGANISM: BOVINE

<400> SEQUENCE: 36

Pro Asn Pro Ile
1

<210> SEQ ID NO 37
<211> LENGTH: 6
<212> TYPE: PRT
<213> ORGANISM: BOVINE

<400> SEQUENCE: 37

Pro Asn Ser Leu Pro Gln
1               5

<210> SEQ ID NO 38
<211> LENGTH: 8
<212> TYPE: PRT
```

<213> ORGANISM: BOVINE

<400> SEQUENCE: 38

Pro Gln Leu Glu Ile Val Pro Asn
1               5

<210> SEQ ID NO 39
<211> LENGTH: 7
<212> TYPE: PRT
<213> ORGANISM: BOVINE

<400> SEQUENCE: 39

Pro Gln Asn Ile Pro Pro Leu
1               5

<210> SEQ ID NO 40
<211> LENGTH: 6
<212> TYPE: PRT
<213> ORGANISM: BOVINE

<400> SEQUENCE: 40

Pro Val Leu Gly Pro Val
1               5

<210> SEQ ID NO 41
<211> LENGTH: 4
<212> TYPE: PRT
<213> ORGANISM: BOVINE

<400> SEQUENCE: 41

Pro Val Pro Gln
1

<210> SEQ ID NO 42
<211> LENGTH: 5
<212> TYPE: PRT
<213> ORGANISM: BOVINE

<400> SEQUENCE: 42

Pro Val Val Val Pro
1               5

<210> SEQ ID NO 43
<211> LENGTH: 6
<212> TYPE: PRT
<213> ORGANISM: BOVINE

<400> SEQUENCE: 43

Pro Val Val Val Pro Pro
1               5

<210> SEQ ID NO 44
<211> LENGTH: 11
<212> TYPE: PRT
<213> ORGANISM: BOVINE

<400> SEQUENCE: 44

Ser Ile Gly Ser Ser Glu Glu Ser Ala Glu
1               5                   10

<210> SEQ ID NO 45
<211> LENGTH: 7
<212> TYPE: PRT
<213> ORGANISM: BOVINE

```
<400> SEQUENCE: 45

Ser Ile Ser Ser Ser Glu Glu
1               5

<210> SEQ ID NO 46
<211> LENGTH: 11
<212> TYPE: PRT
<213> ORGANISM: BOVINE

<400> SEQUENCE: 46

Ser Ile Ser Ser Ser Glu Glu Ile Val Pro Asn
1               5                   10

<210> SEQ ID NO 47
<211> LENGTH: 7
<212> TYPE: PRT
<213> ORGANISM: BOVINE

<400> SEQUENCE: 47

Ser Lys Asp Ile Gly Ser Glu
1               5

<210> SEQ ID NO 48
<211> LENGTH: 6
<212> TYPE: PRT
<213> ORGANISM: BOVINE

<400> SEQUENCE: 48

Ser Pro Pro Glu Ile Asn
1               5

<210> SEQ ID NO 49
<211> LENGTH: 7
<212> TYPE: PRT
<213> ORGANISM: BOVINE

<400> SEQUENCE: 49

Ser Pro Pro Glu Ile Asn Thr
1               5

<210> SEQ ID NO 50
<211> LENGTH: 7
<212> TYPE: PRT
<213> ORGANISM: BOVINE

<400> SEQUENCE: 50

Thr Asp Ala Pro Ser Phe Ser
1               5

<210> SEQ ID NO 51
<211> LENGTH: 5
<212> TYPE: PRT
<213> ORGANISM: BOVINE

<400> SEQUENCE: 51

Thr Glu Asp Glu Leu
1               5

<210> SEQ ID NO 52
<211> LENGTH: 6
<212> TYPE: PRT
<213> ORGANISM: BOVINE

<400> SEQUENCE: 52
```

```
Val Ala Thr Glu Glu Val
1               5

<210> SEQ ID NO 53
<211> LENGTH: 5
<212> TYPE: PRT
<213> ORGANISM: BOVINE

<400> SEQUENCE: 53

Val Leu Pro Val Pro
1               5

<210> SEQ ID NO 54
<211> LENGTH: 4
<212> TYPE: PRT
<213> ORGANISM: BOVINE

<400> SEQUENCE: 54

Val Pro Gly Glu
1

<210> SEQ ID NO 55
<211> LENGTH: 6
<212> TYPE: PRT
<213> ORGANISM: BOVINE

<400> SEQUENCE: 55

Val Pro Gly Glu Ile Val
1               5

<210> SEQ ID NO 56
<211> LENGTH: 6
<212> TYPE: PRT
<213> ORGANISM: BOVINE

<400> SEQUENCE: 56

Val Pro Ile Thr Pro Thr
1               5

<210> SEQ ID NO 57
<211> LENGTH: 4
<212> TYPE: PRT
<213> ORGANISM: BOVINE

<400> SEQUENCE: 57

Val Pro Ser Glu
1

<210> SEQ ID NO 58
<211> LENGTH: 9
<212> TYPE: PRT
<213> ORGANISM: BOVINE

<400> SEQUENCE: 58

Val Val Pro Pro Phe Leu Gln Pro Glu
1               5

<210> SEQ ID NO 59
<211> LENGTH: 5
<212> TYPE: PRT
<213> ORGANISM: BOVINE

<400> SEQUENCE: 59

Val Val Val Pro Pro
1               5
```

```
<210> SEQ ID NO 60
<211> LENGTH: 6
<212> TYPE: PRT
<213> ORGANISM: BOVINE

<400> SEQUENCE: 60

Tyr Pro Phe Pro Gly Pro
1               5

<210> SEQ ID NO 61
<211> LENGTH: 8
<212> TYPE: PRT
<213> ORGANISM: BOVINE

<400> SEQUENCE: 61

Tyr Pro Phe Pro Gly Pro Ile Pro
1               5

<210> SEQ ID NO 62
<211> LENGTH: 9
<212> TYPE: PRT
<213> ORGANISM: BOVINE

<400> SEQUENCE: 62

Tyr Pro Phe Pro Gly Pro Ile Pro Asn
1               5

<210> SEQ ID NO 63
<211> LENGTH: 5
<212> TYPE: PRT
<213> ORGANISM: BOVINE

<400> SEQUENCE: 63

Tyr Pro Ser Gly Ala
1               5

<210> SEQ ID NO 64
<211> LENGTH: 5
<212> TYPE: PRT
<213> ORGANISM: BOVINE

<400> SEQUENCE: 64

Tyr Pro Val Glu Pro
1               5
```

NUTRITIONAL COMPOSITION CONTAINING A PEPTIDE COMPONENT WITH ANTI-INFLAMMATORY PROPERTIES AND USES THEREOF

RELATED APPLICATIONS

This application is a divisional application of copending and commonly assigned U.S. patent application having Ser. No. 13/833,094 filed Mar. 15, 2013 and entitled "Nutritional Compositions Containing A Peptide Component With Anti-InflammatoryProperties And Uses Thereof", the disclosure of which is incorporated by reference herein.

TECHNICAL FIELD

The present disclosure relates to nutritional compositions comprising a peptide component, wherein the peptide component comprises a combination of selected peptides. In certain embodiments, the nutritional compositions reduce an inflammatory response when administered to a subject. More specifically, the nutritional compositions disclosed herein may reduce the production of proinflammatory cytokines, such as Interleukin-17 (hereinafter "IL-17"). The nutritional compositions described herein may be formulated for adult and pediatric subjects.

BACKGROUND

Cytokines are cell-signaling, immunomodulating, proteins that are secreted by a variety of cell types and are used extensively for intercellular communication. Almost all nucleated cells, but especially endothelial and epithelial cells and their resident macrophages, are potent producers of cytokines. Proinflammatory cytokines include interleukin-12 ("IL-12"), interleukin-11 ("IL-11"), interleukin-17 ("IL-17), interleukin-18 ("IL-18), interleukin-5 "(IL-5"), interleukin-4 ("IL-4"), interferon-gamma ("IFN-γ"), interleukin-8 ("IL-8"), tumer necrosis factor alpha ("TNF-α"), tumer necrosis factor beta ("TNF-β"), interleukin 6 ("IL-6"), interleukin-1 ("IL-1"), interleukin-20 ("IL-20"), interleukin-33 ("IL-33"), leukocyte inhibitory factor ("LIF"), oncostatin M ("OSM"), ciliary neurotrophic factor ("CNTF"), transforming growth factor-beta ("TGF-β"), granulocyte-macrophage colony ("GM-CSF"). In particular, IL-17 is a cytokine that acts as a mediator in delayed-type reactions by increasing chemokine production in various tissues to recruit monocytes and neutrophils to the site of inflammation. IL-17 is produced by T-helper cells and is induced by IL-23, which results in destructive tissue damages in delayed-type reactions. IL-17 functions as a proinflammatory cytokine that responds to the invasion of the immune system by extracellular pathogens and induces destruction of the pathogen's cellular matrix.

Immune regulatory functions have been reported for the IL-17 family of cytokines, perhaps due to the fact that IL-17 cytokines induce many immune signaling molecules. IL-17 is involved in inducing and mediating proinflammatory responses. Additionally, IL-17 is associated with allergic responses, as it induces the production of many other cytokines including, but not limited to, IL-6, B-CSF, GM-CSF, IL-1β, TGF-β, TNF-α, chemokines, including IL-8, GRO-α, and MCP-1, and prostaglandins, such as $PGE_2$. IL-17 includes the production of these proinflammatory compounds in a variety of cell types including fibroblasts, endothelial cells, epithelial cells, keratinocytes, and macrophages.

Due to its ability to induce the inflammatory response, IL-17 has been linked to many immune and autoimmune related diseases. Inflammatory conditions mediated by IL-17 include asthma, allergies, skin conditions such as dermatitis, psoriasis and eczema, inflammatory bowel disease, and arthritis. Traditional medications used to treat autoimmune diseases attempt to stop the inflammation involved in the autoimmune attack. However, many of these medications also suppress the ability of the immune system to fight infection and have, potentially, many serious side effects. Furthermore, the inflammatory response plays a significant role in the onset of certain neonatal and childhood diseases.

Accordingly, there is a need for safe, yet effective, nutritional compositions that reduce the inflammatory response in a subject. More particularly, there is a need for infant formulas that reduce the inflammatory response in an infant, and thereby help reduce the onset of certain neonatal and childhood diseases without substantially altering the ability of the immune system to fight infection, and do not produce unwanted side effects when consumed.

BRIEF SUMMARY

Briefly, the present disclosure is directed, in an embodiment, to a nutritional composition comprising a carbohydrate source, a protein equivalent source, and a fat source, wherein the protein equivalent source comprises a peptide component including selected peptides from Table 1 disclosed below. In some embodiments, 20% to 80% of the protein equivalent source includes a peptide component comprising SEQ ID NO 4, SEQ ID NO 13, SEQ ID NO 17, SEQ ID NO 21, SEQ ID NO 24, SEQ ID NO 30, SEQ ID NO 31, SEQ ID NO 32, SEQ ID NO 51, SEQ ID NO 57, SEQ ID NO 60, and SEQ ID NO 63; and 20% to 80% of the protein equivalent source comprises an intact protein, a partially hydrolyzed protein, or a combination thereof.

In another embodiment, the nutritional composition comprises a carbohydrate source, a protein equivalent source, and a fat source, wherein the protein equivalent source comprises at least 3 peptides selected from the group consisting of SEQ ID NO 4, SEQ ID NO 13, SEQ ID NO 17, SEQ ID NO 21, SEQ ID NO 24, SEQ ID NO 30, SEQ ID NO 31, SEQ ID NO 32, SEQ ID NO 51, SEQ ID NO 57, SEQ ID NO 60, and SEQ ID NO 63, and at least 5 additional peptides selected from Table 1; and wherein 20% to 80% of the protein equivalent source comprises an intact protein, a partially hydrolyzed protein, or combinations thereof.

In certain embodiments, the nutritional composition is an pediatric nutritional composition, such as an infant formula or a growing-up milk, an adult nutritional composition, or a nutritional supplement.

The nutritional compositions disclosed herein are, in some embodiments, capable of reducing a proinflammatory response in a subject. For example, when administered to a subject, the nutritional composition reduced the production of proinflammatory cytokines, such as interleukin 12 ("IL-12", IL17, interleukin 5 "(IL-5"), interleukin 4 ("IL-4"), interferon-gamma ("IFN-γ"), interleukin 8 ("IL-8"), tumor necrosis factor alpha ("TNF-α"), interleukin 6 ("IL-6") and interleukin ("IL-1"). Accordingly, in some embodiments the disclosure is directed to a method for reducing the proinflammatory response in a subject, comprising administering to a subject a nutritional composition as described herein.

It is to be understood that both the foregoing general description and the following detailed description present embodiments of the disclosure and are intended to provide an overview or framework for understanding the nature and character of the disclosure as it is claimed. The description serves to explain the principles and operations of the claimed subject matter. Other and further features and advantages of the present disclosure will be readily apparent to those skilled in the art upon a reading of the following disclosure.

DETAILED DESCRIPTION

Reference now will be made in detail to the embodiments of the present disclosure, one or more examples of which are set forth hereinbelow. Each example is provided by way of explanation of the nutritional composition of the present disclosure and is not a limitation. In fact, it will be apparent to those skilled in the art that various modifications and variations can be made to the teachings of the present disclosure without departing from the scope of the disclosure. For instance, features illustrated or described as part of one embodiment, can be used with another embodiment to yield a still further embodiment.

Thus, it is intended that the present disclosure covers such modifications and variations as come within the scope of the appended claims and their equivalents. Other objects, features and aspects of the present disclosure are disclosed in or are apparent from the following detailed description. It is to be understood by one of ordinary skill in the art that the present discussion is a description of exemplary embodiments only and is not intended as limiting the broader aspects of the present disclosure.

"Nutritional composition" means a substance or formulation that satisfies at least a portion of a subject's nutrient requirements. The terms "nutritional(s)", "nutritional formula(s)", "enteral nutritional(s)", and "nutritional supplement (s)" are used as non-limiting examples of nutritional composition(s) throughout the present disclosure. Moreover, "nutritional composition(s)" may refer to liquids, powders, gels, pastes, solids, concentrates, suspensions, or ready-to-use forms of enteral formulas, oral formulas, formulas for infants, formulas for pediatric subjects, formulas for children, growing-up milks and/or formulas for adults. The term "enteral" means deliverable through or within the gastrointestinal, or digestive, tract. "Enteral administration" includes oral feeding, intragastric feeding, transpyloric administration, or any other administration into the digestive tract. "Administration" is broader than "enteral administration" and includes parenteral administration or any other route of administration by which a substance is taken into a subject's body.

The term "medical food" refers enteral compositions that are formulated or intended for the dietary management of a disease or disorder. A medical food may be a food for oral ingestion or tube feeding (nasogastric tube), may be labeled for the dietary management of a specific medical disorder, disease or condition for which there are distinctive nutritional requirements, and may be intended to be used under medical supervision.

The term "peptide" as used herein describes linear molecular chains of amino acids, including single chain molecules or their fragments. The peptides described herein include no more than 50 total amino acids. Peptides may further form oligomers or multimers consisting of at least two identical or different molecules. Furthermore, peptidomimetics of such peptides where amino acid(s) and/or peptide bond(s) have been replaced by functional analogs are also encompassed by the term "peptide". Such functional analogues may include, but are not limited to, all known amino acids other than the 20 gene-encoded amino acids such as selenocysteine.

The term "peptide" may also refer to naturally modified peptides where the modification is effected, for example, by glycosylation, acetylation, phosphorylation and similar modification which are well known in the art. In some embodiments, the peptide component is distinguished from a protein source also disclosed herein. Further, peptides may, for example, be produced recombinantly, semi-synthetically, synthetically, or obtained from natural sources such as after hydrolysation of proteins, including but not limited to casein, all according to methods known in the art.

The term "degree of hydrolysis" refers to the extent to which peptide bonds are broken by a hydrolysis method. For example, the protein equivalent source of the present disclosure may, in some embodiments comprise a protein having a degree of hydrolysis of no greater than 40%.

The term "partially hydrolyzed" means having a degree of hydrolysis which is greater than 0% but less than 50%.

The term "extensively hydrolyzed" means having a degree of hydrolysis which is greater than or equal to 50%.

The term "molar mass distribution" when used in reference to a hydrolyzed protein or protein hydrolysate pertains to the molar mass of each peptide present in the protein hydrolysate. For example, a protein hydrolysate having a molar mass distribution of greater than 500 Daltons means that each peptide included in the protein hydrolysate has a molar mass of at least 500 Daltons. Accordingly, in some embodiments, the peptides disclosed in Table 1 and Table 2 are derived from a protein hydrolysate having a molar mass distribution of greater than 500 Daltons. To produce a protein hydrolysate having a molar mass distribution of greater than 500 Daltons, a protein hydrolysate may be subjected to certain filtering procedures or any other procedure known in the art for removing peptides, amino acids, and/or other proteinaceous material having a molar mass of less than 500 Daltons. For the purposes of this disclosure, any method known in the art may be used to produce the protein hydrolysate having a molar mass distribution of greater than 500 Dalton.

The term "protein equivalent" or "protein equivalent source" includes any protein source, such as soy, egg, whey, or casein, as well as non-protein sources, such as peptides or amino acids. Further, the protein equivalent source can be any used in the art, e.g., nonfat milk, whey protein, casein, soy protein, hydrolyzed protein, peptides, amino acids, and the like. Bovine milk protein sources useful in practicing the present disclosure include, but are not limited to, milk protein powders, milk protein concentrates, milk protein isolates, nonfat milk solids, nonfat milk, nonfat dry milk, whey protein, whey protein isolates, whey protein concentrates, sweet whey, acid whey, casein, acid casein, caseinate (e.g. sodium caseinate, sodium calcium caseinate, calcium caseinate), soy bean proteins, and any combinations thereof. The protein equivalent source can, in some embodiments comprise hydrolyzed protein, including partially hydrolyzed protein and extensively hydrolyzed protein. The protein equivalent source may, in some embodiments, include intact protein. More particularly, the protein source may include a) about 20% to about 80% of the peptide component described herein, and b) about 20% to about 80% of an intact protein, a hydrolyzed protein, or a combination thereof.

The term "protein equivalent source" also encompasses free amino acids. In some embodiments, the amino acids may comprise, but are not limited to, histidine, isoleucine, leucine, lysine, methionine, cysteine, phenylalanine, tyrosine, threonine, tryptophan, valine, alanine, arginine, asparagine, aspartic acid, glutamic acid, glutamine, glycine, proline, serine, carnitine, taurine and mixtures thereof. In some embodiments, the amino acids may be branched chain amino acids. In certain other embodiments, small amino acid peptides may be included as the protein component of the nutritional composition. Such small amino acid peptides may be naturally occurring or synthesized.

"Pediatric subject" means a human less than 13 years of age. In some embodiments, a pediatric subject refers to a human subject that is between birth and 8 years old. In other embodiments, a pediatric subject refers to a human subject between 1 and 6 years of age. In still further embodiments, a pediatric subject refers to a human subject between 6 and 12 years of age. The term "pediatric subject" may refer to infants (preterm or full term) and/or children, as described below.

"Infant" means a human subject ranging in age from birth to not more than one year and includes infants from 0 to 12 months corrected age. The phrase "corrected age" means an infant's chronological age minus the amount of time that the infant was born premature. Therefore, the corrected age is the age of the infant if it had been carried to full term. The term infant includes low birth weight infants, very low birth weight infants, and preterm infants. "Preterm" means an infant born before the end of the 37$^{th}$ week of gestation. "Full term" means an infant born after the end of the 37$^{th}$ week of gestation.

"Child" means a subject ranging in age from 12 months to about 13 years. In some embodiments, a child is a subject between the ages of 1 and 12 years old. In other embodiments, the terms "children" or "child" refer to subjects that are between one and about six years old, or between about seven and about 12 years old. In other embodiments, the terms "children" or "child" refer to any range of ages between 12 months and about 13 years.

"Children's nutritional product" refers to a composition that satisfies at least a portion of the nutrient requirements of a child. A growing-up milk is an example of a children's nutritional product.

"Infant formula" means a composition that satisfies at least a portion of the nutrient requirements of an infant. In the United States, the content of an infant formula is dictated by the federal regulations set forth at 21 C.F.R. Sections 100, 106, and 107. These regulations define macronutrient, vitamin, mineral, and other ingredient levels in an effort to simulate the nutritional and other properties of human breast milk.

The term "growing-up milk" refers to a broad category of nutritional compositions intended to be used as a part of a diverse diet in order to support the normal growth and development of a child between the ages of about 1 and about 6 years of age.

"Nutritionally complete" means a composition that may be used as the sole source of nutrition, which would supply essentially all of the required daily amounts of vitamins, minerals, and/or trace elements in combination with proteins, carbohydrates, and lipids. Indeed, "nutritionally complete" describes a nutritional composition that provides adequate amounts of carbohydrates, lipids, essential fatty acids, proteins, essential amino acids, conditionally essential amino acids, vitamins, minerals and energy required to support normal growth and development of a subject.

Therefore, a nutritional composition that is "nutritionally complete" for a preterm infant will, by definition, provide qualitatively and quantitatively adequate amounts of carbohydrates, lipids, essential fatty acids, proteins, essential amino acids, conditionally essential amino acids, vitamins, minerals, and energy required for growth of the preterm infant.

A nutritional composition that is "nutritionally complete" for a full term infant will, by definition, provide qualitatively and quantitatively adequate amounts of all carbohydrates, lipids, essential fatty acids, proteins, essential amino acids, conditionally essential amino acids, vitamins, minerals, and energy required for growth of the full term infant.

A nutritional composition that is "nutritionally complete" for a child will, by definition, provide qualitatively and quantitatively adequate amounts of all carbohydrates, lipids, essential fatty acids, proteins, essential amino acids, conditionally essential amino acids, vitamins, minerals, and energy required for growth of a child.

As applied to nutrients, the term "essential" refers to any nutrient that cannot be synthesized by the body in amounts sufficient for normal growth and to maintain health and that, therefore, must be supplied by the diet. The term "conditionally essential" as applied to nutrients means that the nutrient must be supplied by the diet under conditions when adequate amounts of the precursor compound is unavailable to the body for endogenous synthesis to occur.

"Prebiotic" means a non-digestible food ingredient that beneficially affects the host by selectively stimulating the growth and/or activity of one or a limited number of bacteria in the digestive tract that can improve the health of the host.

"Probiotic" means a microorganism with low or no pathogenicity that exerts at least one beneficial effect on the health of the host.

The term "inactivated probiotic" means a probiotic wherein the metabolic activity or reproductive ability of the referenced probiotic organism has been reduced or destroyed. The "inactivated probiotic" does, however, still retain, at the cellular level, at least a portion its biological glycol-protein and DNA/RNA structure. As used herein, the term "inactivated" is synonymous with "non-viable". More specifically, a non-limiting example of an inactivated probiotic is inactivated *Lactobacillus rhamnosus* GG ("LGG") or "inactivated LGG".

All percentages, parts and ratios as used herein are by weight of the total formulation, unless otherwise specified.

The nutritional composition of the present disclosure may be substantially free of any optional or selected ingredients described herein, provided that the remaining nutritional composition still contains all of the required ingredients or features described herein. In this context, and unless otherwise specified, the term "substantially free" means that the selected composition may contain less than a functional amount of the optional ingredient, typically less than 0.1% by weight, and also, including zero percent by weight of such optional or selected ingredient.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods and compositions of the present disclosure, including components thereof, can comprise, consist of, or consist essentially of the essential elements and limitations of the embodiments described herein, as well as any additional or optional ingredients, components or limitations described herein or otherwise useful in nutritional compositions.

As used herein, the term "about" should be construed to refer to both of the numbers specified as the endpoint(s) of any range. Any reference to a range should be considered as providing support for any subset within that range.

The proinflammatory response, or inflammation, is induced by certain stimuli, such as pathogens, damaged cells, or irritants. An inflammatory response can lead to a variety of disorders affecting numerous tissue types, including epithelial, connective, neurologic and intestinal. For example inflammatory responses can lead to or worsen the symptoms of skin disorders (such as psoriasis, eczema and other rashes), inflammatory bowel disease, cystic fibrosis, multiple sclerosis, arthritis (e.g., rheumatoid arthritis), allergies, and even cancer. Inflammatory diseases are becoming more widespread and many have no cure. Accordingly, it would be advantageous to provide nutritional compositions that may be of modulating the proinflammatory response in a subject.

Accordingly, the present disclosure relates generally to nutritional compositions comprising a protein equivalent source, wherein the protein equivalent source includes a peptide component comprising SEQ ID NO 4, SEQ ID NO 13, SEQ ID NO 17, SEQ ID NO 21, SEQ ID NO 24, SEQ ID NO 30, SEQ ID NO 31, SEQ ID NO 32, SEQ ID NO 51, SEQ ID NO 57, SEQ ID NO 60, and SEQ ID NO 63. In some embodiments, the peptide component may comprise additional peptides disclosed in Table 1. For example, the composition may include at least 10 additional peptides disclosed in Table 1. In some embodiments, 20% to 80% of the protein equivalent source comprises the peptide component, and 20% to 80% of the protein equivalent source comprises an intact protein, a partially hydrolyzed protein, and combinations thereof. In some embodiments, the term additional means selecting different peptides than those enumerated.

In another embodiment 20% to 80% of the protein equivalent source includes a peptide component comprising at least 3 peptides selected from the group consisting of SEQ ID NO 4, SEQ ID NO 13, SEQ ID NO 17, SEQ ID NO 21, SEQ ID NO 24, SEQ ID NO 30, SEQ ID NO 31, SEQ ID NO 32, SEQ ID NO 51, SEQ ID NO 57, SEQ ID NO 60, and SEQ ID NO 63, and at least 5 additional peptides selected from Table 1; and wherein 20% to 80% of the protein equivalent source comprises an intact protein, a partially hydrolyzed protein, or combinations thereof.

Table 1 below identifies the amino acid sequences of the peptides that may be included in the peptide component of the present nutritional compositions.

TABLE 1

| Sequence ID Number | Amino Acid Sequence | (aa) |
|---|---|---|
| 1 | Ala Ile Asn Pro Ser Lys Glu Asn | 8 |
| 2 | Ala Pro Phe Pro Glu | 5 |
| 3 | Asp Ile Gly Ser Glu Ser | 6 |
| 4 | Asp Lys Thr Glu Ile Pro Thr | 7 |
| 5 | Asp Met Glu Ser Thr | 5 |
| 6 | Asp Met Pro Ile | 4 |
| 7 | Asp Val Pro Ser | 4 |
| n/a | Glu Asp Ile | 3 |
| n/a | Glu Leu Phe | 3 |
| n/a | Glu Met Pro | 3 |
| 8 | Glu Thr Ala Pro Val Pro Leu | 7 |

TABLE 1-continued

| Sequence ID Number | Amino Acid Sequence | (aa) |
|---|---|---|
| 9 | Phe Pro Gly Pro Ile Pro | 6 |
| 10 | Phe Pro Gly Pro Ile Pro Asn | 7 |
| 11 | Gly Pro Phe Pro | 4 |
| 12 | Gly Pro Ile Val | 4 |
| 13 | Ile Gly Ser Glu Ser Thr Glu Asp Gln | 9 |
| 14 | Ile Gly Ser Ser Ser Glu Glu Ser | 8 |
| 15 | Ile Gly Ser Ser Ser Glu Glu Ser Ala | 9 |
| 16 | Ile Asn Pro Ser Lys Glu | 6 |
| 17 | Ile Pro Asn Pro Ile | 5 |
| 18 | Ile Pro Asn Pro Ile Gly | 6 |
| 19 | Ile Pro Pro Leu Thr Gln Thr Pro Val | 9 |
| 20 | Ile Thr Ala Pro | 4 |
| 21 | Ile Val Pro Asn | 4 |
| 22 | Lys His Gln Gly Leu Pro Gln | 7 |
| 23 | Leu Asp Val Thr Pro | 5 |
| 24 | Leu Glu Asp Ser Pro Glu | 6 |
| 25 | Leu Pro Leu Pro Leu | 5 |
| 26 | Met Glu Ser Thr Glu Val | 6 |
| 27 | Met His Gln Pro His Gln Pro Leu Pro Pro Thr | 11 |
| 28 | Asn Ala Val Pro Ile | 5 |
| 29 | Asn Glu Val Glu Ala | 5 |
| n/a | Asn Leu Leu | 3 |
| 30 | Asn Gln Glu Gln Pro Ile | 6 |
| 31 | Asn Val Pro Gly Glu | 5 |
| 32 | Pro Phe Pro gly Pro Ile | 6 |
| 33 | Pro Gly Pro Ile Pro Asn | 6 |
| 34 | Pro His Gln Pro Leu Pro Pro Thr | 8 |
| 35 | Pro Ile Thr Pro Thr | 5 |
| 36 | Pro Asn Pro Ile | 4 |
| 37 | Pro Asn Ser Leu Pro Gln | 6 |
| 38 | Pro Gln Leu Glu Ile Val Pro Asn | 8 |
| 39 | Pro Gln Asn Ile Pro Pro Leu | 7 |
| 40 | Pro Val Leu Gly Pro Val | 6 |
| 41 | Pro Val Pro Gln | 4 |
| 42 | Pro Val Val Val Pro | 5 |
| 43 | Pro Val Val Val Pro Pro | 6 |
| 44 | Ser Ile Gly Ser Ser Ser Glu Glu Ser Ala Glu | 11 |
| 45 | Ser Ile Ser Ser Ser Glu Glu | 7 |
| 46 | Ser Ile Ser Ser Ser Glu Glu Ile Val Pro Asn | 11 |
| 47 | Ser Lys Asp Ile Gly Ser Glu | 7 |
| 48 | Ser Pro Pro Glu Ile Asn | 6 |
| 49 | Ser Pro Pro Glu Ile Asn Thr | 7 |
| 50 | Thr Asp Ala Pro Ser Phe Ser | 7 |
| 51 | Thr Glu Asp Glu Leu | 5 |
| 52 | Val Ala Thr Glu Glu Val | 6 |
| 53 | Val Leu Pro Val Pro | 5 |
| 54 | Val Pro Gly Glu | 4 |
| 55 | Val Pro Gly Glu Ile Val | 6 |
| 56 | Val Pro Ile Thr Pro Thr | 6 |
| 57 | Val Pro Ser Glu | 4 |
| 58 | Val Val Pro Pro Phe Leu Gln Pro Glu | 9 |
| 59 | Val Val Val Pro Pro | 5 |
| 60 | Tyr Pro Phe Pro Gly Pro | 6 |
| 61 | Tyr Pro Phe Pro Gly Pro Ile Pro | 8 |
| 62 | Tyr Pro Phe Pro Gly Pro Ile Pro Asn | 9 |
| 63 | Tyr Pro Ser Gly Ala | 5 |
| 64 | Tyr Pro Val Glu Pro | 5 |

Table 2 below further identifies a subset of amino acid sequences from Table 1 that may be included in the peptide component disclosed herein.

TABLE 2

| Sequence ID Number | Amino Acid Sequence | (aa) |
|---|---|---|
| 4 | Asp Lys Thr Glu Ile Pro Thr | 7 |
| 13 | Ile Gly Ser Glu Ser Thr Glu Asp Gln | 9 |
| 17 | Ile Pro Asn Pro Ile Gly | 6 |
| 21 | Ile Val Pro Asn | 4 |
| 24 | Leu Glu Asp Ser Pro Glu | 6 |
| 30 | Asn Gln Glu Gln Pro Ile | 6 |

TABLE 2-continued

| Sequence ID Number | Amino Acid Sequence | (aa) |
|---|---|---|
| 31 | Asn Val Pro Gly Glu | 5 |
| 32 | Pro Phe Pro Gly Pro Ile | 6 |
| 51 | Thr Glu Asp Glu Leu | 5 |
| 57 | Val Pro Ser Glu | 4 |
| 60 | Tyr Pro Phe Pro Gly Pro | 6 |
| 63 | Tyr Pro Ser Gly Ala | 5 |

In some embodiments, the peptide component may be present in the nutritional composition in an amount from about 0.2 g/100 kcal to about 5.6 g/100 kcal. In other embodiments the peptide component may be present in the nutritional composition in an amount from about 1 g/100 kcal to about 4 g/100 kcal. In still other embodiments, the peptide component may be present in the nutritional composition in an amount from about 2 g/100 kcal to about 3 g/100 kcal.

The peptide component disclosed herein may be formulated with other ingredients in the nutritional composition to provide appropriate nutrient levels for the target subject. In some embodiments, the peptide component is included in a nutritionally complete formula that is suitable to support normal growth.

In other embodiments, the peptide component may comprise a nutritional supplement or additive that may be added to other nutritional formulations including, but not limited to, foodstuffs and/or beverages. For the purposes of this disclosure, "nutritional supplement" includes a concentrated source of nutrient, for example the peptides identified herein, or alternatively other substances with a nutritional or physiological effective whose purpose is to supplement the normal diet.

The peptide component may be provided as an element of a protein equivalent source. In some embodiments, the peptides identified in Tables 1 and 2, may be provided by a protein equivalent source obtained from cow's milk proteins, including but not limited to bovine casein and bovine whey. In some embodiments, the protein equivalent source comprises hydrolyzed bovine casein or hydrolyzed bovine whey. Accordingly, in some embodiments, the peptides identified in Table 1 and Table 2 may be provided by a casein hydrolysate. Such peptides may be obtained by hydrolysis or may be synthesized in vitro by methods know to the skilled person. A nonlimiting example of a method of hydrolysis utilizing a proteolytic enzyme is disclosed in U.S. Pat. No. 7,618,669 to Rangavajla et al., which is hereby incorporated by reference in its entirety; however, other methods of hydrolysis may be used in practice of the present disclosure.

In some embodiments, the protein equivalent source comprises a hydrolyzed protein, which includes partially hydrolyzed protein and extensively hydrolyzed protein, such as casein. In some embodiments, protein equivalent source comprises a hydrolyzed protein including peptides having a molar mass distribution of greater than 500 Daltons. In some embodiments, the hydrolyzed protein comprises peptides having a molar mass distribution in the range of from about 500 Daltons to about 1,500 Daltons. Still, in some embodiments the hydrolyzed protein may comprise peptides having a molar mass distribution range of from about 500 Daltons to about 2,000 Daltons.

In some embodiments, the protein equivalent source may comprise the peptide component, intact protein, hydrolyzed protein, including partially hydrolyzed protein, and combinations thereof. In some embodiments, 20% to 80% of the protein equivalent source comprises the peptide component disclosed herein. In some embodiments, 30% to 60% of the protein equivalent source comprises the peptide component disclosed herein. In still other embodiments, 40% to 50% of the protein equivalent source comprises the peptide component.

In some embodiments, 20% to 80% of the protein equivalent source comprises intact protein, partially hydrolyzed protein, or combinations thereof. In some embodiments, 40% to 70% of the protein equivalent source comprises intact proteins, partially hydrolyzed proteins, or a combination thereof. In still further embodiments, 50% to 60% of the protein equivalent source may comprise intact proteins, partially hydrolyzed protein, or a combination thereof.

In some embodiments the protein equivalent source comprises partially hydrolyzed protein having a degree of hydrolysis of less than 40%. In still other embodiments, the protein equivalent source may comprise partially hydrolyzed protein having a degree of hydrolysis of less than 25%, or less than 15%.

In some embodiments, the nutritional composition comprises between about 1 g and about 7 g of a protein equivalent source per 100 kcal. In other embodiments, the nutritional composition comprises between about 3.5 g and about 4.5 g of protein equivalent source per 100 kcal.

Additionally, the protein equivalent source including the peptide component may be added or incorporated into the nutritional composition by any method well known in the art. In some embodiments, the peptide component may be added to a nutritional composition to supplement the nutritional composition. For example, in one embodiment, the peptide component may be added to a commercially available infant formula. For example, Enfalac, Enfamil®, Enfamil® Premature Formula, Enfamil® with Iron, Enfamil® LIPIL®, Lactofree®, Nutramigen®, Pregestimil®, and ProSobee® (available from Mead Johnson & Company, Evansville, Ind., U.S.A.) may be supplemented with suitable levels of the peptide component, and used in practice of the present disclosure.

The nutritional composition(s) of the present disclosure including the peptide component, may be administered in one or more doses daily. Any orally acceptable dosage form is contemplated by the present disclosure. Examples of such dosage forms include, but are not limited to pills, tablets, capsules, soft-gels, liquids, liquid concentrates, powders, elixirs, solutions, suspensions, emulsions, lozenges, beads, cachets, and combinations thereof.

In some embodiments, the peptide component may be added to a more complete nutritional product. In this embodiment, the nutritional composition may contain protein, fat, and carbohydrate components and may be used to supplement the diet or may be used as the sole source of nutrition.

In some embodiments, the nutritional composition comprises at least one carbohydrate source. The carbohydrate source can be any used in the art, e.g., lactose, glucose, fructose, corn syrup solids, maltodextrins, sucrose, starch, rice syrup solids, and the like. The amount of the carbohydrate component in the nutritional composition typically can vary from between about 5 g/100 kcal and about 25 g/100 kcal. In some embodiments, the amount of carbohydrate is between about 6 g/100 kcal and about 22 g/100 kcal. In other embodiments, the amount of carbohydrate is between about 12 g/100 kcal and about 14 g/100 kcal. In some embodiments, corn syrup solids are preferred. Moreover, hydrolyzed, partially hydrolyzed, and/or extensively hydrolyzed carbohydrates may be desirable for inclusion in the nutritional composition due to their easy digestibility. Specifically, hydrolyzed carbohydrates are less likely to contain allergenic epitopes.

Non-limiting examples of carbohydrate materials suitable for use herein include hydrolyzed or intact, naturally or chemically modified, starches sourced from corn, tapioca, rice or potato, in waxy or non-waxy forms. Non-limiting examples of suitable carbohydrates include various hydrolyzed starches characterized as hydrolyzed cornstarch, maltodextrin, maltose, corn syrup, dextrose, corn syrup solids, glucose, and various other glucose polymers and combinations thereof. Non-limiting examples of other suitable carbohydrates include those often referred to as sucrose, lactose, fructose, high fructose corn syrup, indigestible oligosaccharides such as fructooligosaccharides and combinations thereof.

The nutritional composition may be protein-free in some embodiments and comprise free amino acids as an element of the protein equivalent source. In some embodiments, the amino acids may be branched chain amino acids. In certain other embodiments, small amino acid peptides may be included as the protein component of the nutritional composition. Such small amino acid peptides may be naturally occurring or synthesized. The amount of free amino acids in the nutritional composition may vary from about 1 g/100 kcal to about 5 g/100 kcal.

The nutritional composition may also comprise a fat source. Suitable fat or lipid sources for the nutritional composition of the present disclosure may be any known or used in the art, including but not limited to, animal sources, e.g., milk fat, butter, butter fat, egg yolk lipid; marine sources, such as fish oils, marine oils, single cell oils; vegetable and plant oils, such as corn oil, canola oil, sunflower oil, soybean oil, palm olein oil, coconut oil, high oleic sunflower oil, evening primrose oil, rapeseed oil, olive oil, flaxseed (linseed) oil, cottonseed oil, high oleic safflower oil, palm stearin, palm kernel oil, wheat germ oil; medium chain triglyceride oils and emulsions and esters of fatty acids; and any combinations thereof.

In some embodiment the nutritional composition comprises between about 1.3 g/100 kcal to about 7.2 g/100 kcal of a fat source. In other embodiments the fat source may be present in an amount from about 2.5 g/100 kcal to about 6.0 g/100 kcal. In still other embodiments, the fat source may be present in the nutritional composition in an amount from about 3.0 g/100 kcal to about 4.0 g/100 kcal.

The nutritional composition of the present disclosure may also contain a source of long chain polyunsaturated fatty acids ("LCPUFAs"). Suitable LCPUFAs include, but are not limited to DHA, eicosapentaenoic acid ("EPA"), ARA, linoleic (18:2 n-6), γ-linolenic (18:3 n-6), dihomo-γ-linolenic (20:3 n-6) acids in the n-6 pathway, α-linolenic (18:3 n-3), stearidonic (18:4 n-3), eicosatetraenoic (20:4 n-3), eicosapentaenoic (20:5 n-3), and docosapentaenoic (22:6 n-3).

The amount of LCPUFA in the nutritional composition is at least about 5 mg/100 kcal, and may vary from about 5 mg/100 kcal to about 100 mg/100 kcal, more preferably from about 10 mg/100 kcal to about 50 mg/100 kcal.

Sources of LCPUFAs include dairy products like eggs and butterfat; marine oils, such as cod, menhaden, sardine, tuna and many other fish; certain animal fats, lard, tallow and microbial oils such as fungal and algal oils, or from any other resource fortified or not, form which LCPUFAs could be obtained and used in a nutritional composition. The LCPUFA could be part of a complex mixture obtained by separation technology known in the art aimed at enrichment of LCPUFAs and the derivatives or precursors of LCPUFAs in such mixtures.

The LCPUFAs may be provided in the nutritional composition in the form of esters of free fatty acids; mono-, di- and tri-glycerides; phosphoglycerides, including lecithins; and/or mixtures thereof. Additionally, LCPUFA may be provided in the nutritional composition in the form of phospholipids, especially phosphatidylcholine.

In an embodiment, especially if the nutritional composition is an infant formula, the nutritional composition is supplemented with both DHA and ARA. In this embodiment, the weight ratio of ARA:DHA may be between about 1:3 and about 9:1. In a particular embodiment, the weight ratio of ARA:DHA is from about 1:2 to about 4:1.

DHA is advantageously present in the nutritional composition, in some embodiments, from at least about 17 mg/100 kcal, and may vary from about 5 mg/100 kcal to about 75 mg/100 kcal. In some embodiments, DHA is present from about 10 mg/100 kcal to about 50 mg/100 kcal.

The nutritional composition may be supplemented with oils containing DHA and/or ARA using standard techniques known in the art. For example, DHA and ARA may be added to the composition by replacing an equivalent amount of an oil, such as high oleic sunflower oil, normally present in the composition. As another example, the oils containing DHA and ARA may be added to the composition by replacing an equivalent amount of the rest of the overall fat blend normally present in the composition without DHA and ARA.

If utilized, the source of DHA and/or ARA may be any source known in the art such as marine oil, fish oil, single cell oil, egg yolk lipid, and brain lipid. In some embodiments, the DHA and ARA are sourced from single cell Martek oils, DHASCO® and ARASCO®, or variations thereof. The DHA and ARA can be in natural form, provided that the remainder of the LCPUFA source does not result in any substantial deleterious effect on the infant. Alternatively, the DHA and ARA can be used in refined form.

In an embodiment, sources of DHA and ARA are single cell oils as taught in U.S. Pat. Nos. 5,374,567; 5,550,156; and 5,397,591, the disclosures of which are incorporated herein in their entirety by reference. However, the present disclosure is not limited to only such oils.

Furthermore, some embodiments of the nutritional composition may mimic certain characteristics of human breast milk. However, to fulfill the specific nutrient requirements of some subjects, the nutritional composition may comprise a higher amount of some nutritional components than does human milk. For example, the nutritional composition may comprise a greater amount of DHA than does human breast milk. The enhanced level of DHA of the nutritional composition may compensate for an existing nutritional DHA deficit.

The nutritional composition may also contain one or more prebiotics (also referred to as a prebiotic source) in certain embodiments. Prebiotics can stimulate the growth and/or activity of ingested probiotic microorganisms, selectively reduce pathogens found in the gut, and favorably influence the short chain fatty acid profile of the gut. Such prebiotics may be naturally-occurring, synthetic, or developed through the genetic manipulation of organisms and/or plants, whether such new source is now known or developed later. Prebiotics useful in the present disclosure may include oligosaccharides, polysaccharides, and other prebiotics that contain fructose, xylose, soya, galactose, glucose and mannose.

More specifically, prebiotics useful in the present disclosure may include polydextrose, polydextrose powder, lactulose, lactosucrose, raffinose, gluco-oligosaccharide, inulin, fructo-oligosaccharide, isomalto-oligosaccharide, soybean oligosaccharides, lactosucrose, xylo-oligosaccharide, chito-oligosaccharide, manno-oligosaccharide, aribino-oligosaccharide, siallyl-oligosaccharide, fuco-oligosaccharide, galacto-oligosaccharide, and gentio-oligosaccharides. In some embodiments, the total amount of prebiotics present in the nutritional composition may be from about 0.1 g/100 kcal to about 1 g/100 kcal. In certain embodiments, the total amount of prebiotics present in the nutritional composition may be from about 0.3 g/100 kcal to about 0.7 g/100 kcal. Moreover, the nutritional composition may comprise a prebiotic component comprising polydextrose ("PDX") and/or galacto-oligosaccharide ("GOS"). In some embodiments, the prebiotic component comprises at least 20% GOS, PDX or a mixture thereof.

If PDX is used in the prebiotic composition, the amount of PDX in the nutritional composition may, in an embodiment, be within the range of from about 0.1 g/100 kcal to about 1 g/100 kcal. In another embodiment, the amount of polydextrose is within the range of from about 0.2 g/100 kcal to about 0.6 g/100 kcal. And in still other embodiments, the amount of PDX in the nutritional composition may be from about 0.1 mg/100 kcal to about 0.5 mg/100 kcal.

If GOS is used in the prebiotic composition, the amount of GOS in the nutritional composition may, in an embodiment, be from about 0.1 g/100 kcal to about 1 g/100 kcal. In another embodiment, the amount of GOS in the nutritional composition may be from about 0.2 g/100 kcal to about 0.5 g/100 kcal. In other embodiments, the amount of GOS in the nutritional composition may be from about 0.1 mg/100 kcal to about 1.0 mg/100 kcal or from about 0.1 mg/100 kcal to about 0.5 mg/100 kcal.

In a particular embodiment of the nutritional composition, PDX is administered in combination with GOS. In this embodiment, PDX and GOS can be administered in a ratio of PDX:GOS of between about 9:1 and 1:9. In another embodiment, the ratio of PDX:GOS can be between about 5:1 and 1:5. In yet another embodiment, the ratio of PDX:GOS can be between about 1:3 and 3:1. In a particular embodiment, the ratio of PDX to GOS can be about 5:5. In another particular embodiment, the ratio of PDX to GOS can be about 8:2.

In a particular embodiment, GOS and PDX are supplemented into the nutritional composition in a total amount of at least about 0.2 mg/100 kcal or about 0.2 mg/100 kcal to about 1.5 mg/100 kcal. In some embodiments, the nutritional composition may comprise GOS and PDX in a total amount of from about 0.6 to about 0.8 mg/100 kcal.

In some embodiments, the nutritional composition may contain one or more probiotics. Any probiotic known in the art may be acceptable in this embodiment. In a particular embodiment, the probiotic may be selected from any *Lactobacillus* species, *Lactobacillus rhamnosus* GG (ATCC number 53103), *Bifidobacterium* species, *Bifidobacterium longum* BB536 (BL999, ATCC: BAA-999), *Bifidobacterium longum* AH1206 (NCIMB: 41382), *Bifidobacterium breve* AH1205 (NCIMB: 41387), *Bifidobacterium infantis* 35624 (NCIMB: 41003), and *Bifidobacterium animalis* subsp. *lactis* BB-12 (DSM No. 10140) or any combination thereof.

If included in the composition, the amount of the probiotic may vary from about $1\times10^4$ to about $1.5\times10^{10}$ cfu of probiotics per 100 kcal, more preferably from about $1\times10^6$ to about $1\times10^9$ cfu of probiotics per 100 kcal. In certain other embodiments the amount of probiotic may vary from about $1\times10^7$ cfu/100 kcal to about $1\times10^8$ cfu/100 kcal.

In an embodiment, the probiotic(s) may be viable or non-viable. As used herein, the term "viable", refers to live microorganisms. The term "non-viable" or "non-viable probiotic" means non-living probiotic microorganisms, their cellular components and/or metabolites thereof. Such non-viable probiotics may have been heat-killed or otherwise inactivated, but they retain the ability to favorably influence the health of the host. The probiotics useful in the present disclosure may be naturally-occurring, synthetic or developed through the genetic manipulation of organisms, whether such source is now known or later developed.

In some embodiments, other than a probiotic itself, the nutritional composition(s) of the present disclosure may comprise a culture supernatant from a late-exponential growth phase of a probiotic batch-cultivation process (hereinafter referred to as the "culture supernatant"); in specific embodiments, the probiotic is LGG. Batch cultivation culture supernatant (which can also be referred to as "spent medium") may possesses protection against pathogen infection, including infection by *C. sakazakii*. Specifically the harvested culture supernatant may prevent the invasion of *C. sakazakii* to organs such as the brain and reduce mortality associated with *C. sakazakii*.

In some embodiments, the nutritional composition comprises a culture supernatant from a late-exponential growth phase of a probiotic batch-cultivation process, for use in the treatment or prevention of pathogen infection. In certain embodiments, the probiotic is LGG, and the pathogen is *C. sakazakii*.

Without wishing to be bound by theory, it is believed that the activity of the culture supernatant can be attributed to the mixture of components (including proteinaceous materials, and possibly including (exo)polysaccharide materials) as found released into the culture medium at a late stage of the exponential (or "log") phase of batch cultivation of LGG. The chemical composition of the culture supernatant is believed to be a mixture of a plurality of amino acids, oligo- and polypeptides, and proteins, of various molecular weights. The culture supernatant may further comprise polysaccharide structures and/or nucleotides. In some embodiments the culture supernatant pertains to the entire, i.e. unfractionated culture supernatant. Further, in some embodiments the culture supernatant pertains to the entire, i.e. unfractionated culture supernatant.

The stages recognized in batch cultivation of bacteria are known to the skilled person. These are the "lag," the "log" ("logarithmic" or "exponential"), the "stationary" and the "death" (or "logarithmic decline") phases. In all phases during which live bacteria are present, the bacteria metabolize nutrients from the media, and secrete (exert, release) materials into the culture medium. The composition of the secreted material at a given point in time of the growth stages is not generally predictable.

In some embodiments, a composition according to the disclosure and/or embodiments thereof is obtainable by a process comprising the steps of (a) subjecting a probiotic such as LGG to cultivation in a suitable culture medium using a batch process; (b) harvesting the culture supernatant at a late exponential growth phase of the cultivation step, which phase is defined with reference to the second half of the time between the lag phase and the stationary phase of the batch-cultivation process; (c) optionally removing low molecular weight constituents from the supernatant so as to retain molecular weight constituents above 5 kiloDaltons (kDa) or even above 6 kDa; (d) removing liquid contents from the culture supernatant so as to obtain the composition.

In the present disclosure and embodiments thereof, secreted materials are harvested from a late exponential phase. The late exponential phase occurs in time after the mid exponential phase (which is halftime of the duration of the exponential phase, hence the reference to the late exponential phase as being the second half of the time between the lag phase and the stationary phase). In particular, the term "late exponential phase" is used herein with reference to the latter quarter portion of the time between the lag phase and the stationary phase of the batch-cultivation process. In some embodiments of the present disclosure, harvesting of the culture supernatant is at a point in time of 75% to 85% of the duration of the exponential phase, and most preferably is at about ⅚ of the time elapsed in the exponential phase.

The term "cultivation" or "culturing" refers to the propagation of microorganisms, in this case LGG, on or in a suitable medium. Such a culture medium can be of a variety of kinds, and is particularly a liquid broth, as customary in the art. A preferred broth, e.g., is MRS broth as generally used for the cultivation of lactobacilli. MRS broth generally comprises polysorbate, acetate, magnesium and manganese, which are known to act as special growth factors for lactobacilli, as well as a rich nutrient base. A typical composition comprises (amounts in g/liter): peptone from casein 10.0; meat extract 8.0; yeast extract 4.0; D(+)-glucose 20.0; dipotassium hydrogen phosphate 2.0; Tween® 80 1.0; tri-ammonium citrate 2.0; sodium acetate 5.0; magnesium sulphate 0.2; manganese sulphate 0.04.

In some embodiments, the culture supernatant of the present disclosure may be included in a nutritional composition that is an infant formula. The harvesting of secreted bacterial products brings about a problem that the culture media cannot easily be deprived of undesired components. This specifically relates to nutritional products for relatively vulnerable subjects, such as infant formula or clinical nutrition. This problem is not incurred if specific components from a culture supernatant are first isolated, purified, and then applied in a nutritional product. However, it is desired to make use of a more complete cultural supernatant. This would serve to provide a composition better reflecting the natural action of the probiotic (i.e. LGG). One cannot, however, just use the culture supernatant itself as a basis for non-viable probiotic materials to be specifically used in infant formula and the like.

In some embodiments, the culture supernatant harvested from LGG cultivation does not contain components (as may present in the culture medium) that are not desired, or generally accepted, in nutritional compositions, such as an infant formula. With reference to polysorbate regularly present in MRS broth, media for the culturing of bacteria may include an emulsifying non-ionic surfactant, e.g. on the basis of polyethoxylated sorbitan and oleic acid (typically available as Tween® polysorbates, such as Tween® 80). While these surfactants are frequently found in food products, e.g. ice cream, and are generally recognized as safe, they are not in all jurisdictions considered desirable, or even acceptable for use in nutritional products for relatively vulnerable subjects, such as infant formula or clinical nutrition.

The present disclosure thus, in some embodiments utilizes a culture media in which the aforementioned polysorbates can be avoided. To this end, a culture medium of the disclosure is devoid of polysorbates such as Tween 80. In a preferred embodiment of the disclosure and/or embodiments thereof the culture medium may comprise an oily ingredient selected from the group consisting of oleic acid, linseed oil, olive oil, rape seed oil, sunflower oil and mixtures thereof. It will be understood that the full benefit of the oily ingredient is attained if the presence of a polysorbate surfactant is essentially or entirely avoided.

The culture supernatant, in some embodiments, may have a neutral pH, such as a pH of between pH 5 and pH 7, preferably pH 6.

In addition to the foregoing, it should be noted that the batch cultivation of lactobacilli, including LGG, is common general knowledge available to the person skilled in the art. These methods thus do not require further elucidation here. The culture supernatant of the present disclosure can be harvested by any known technique for the separation of culture supernatant from a bacterial culture. Such techniques are well-known in the art and include, e.g., centrifugation, filtration, sedimentation, and the like.

The disclosed nutritional composition(s) may be provided in any form known in the art, such as a powder, a gel, a suspension, a paste, a solid, a liquid, a liquid concentrate, a reconstituteable powdered milk substitute or a ready-to-use product. The nutritional composition may, in certain embodiments, comprise a nutritional supplement, children's nutritional product, infant formula, human milk fortifier, growing-up milk or any other nutritional composition designed for an infant or a pediatric subject. Nutritional compositions of the present disclosure include, for example, orally-ingestible, health-promoting substances including, for example, foods, beverages, tablets, capsules and powders. Moreover, the nutritional composition of the present disclosure may be standardized to a specific caloric content, it may be provided as a ready-to-use product, or it may be provided in a concentrated form. In some embodiments, the nutritional composition is in powder form with a particle size in the range of 5 μm to 1500 μm, more preferably in the range of 10 μm to 300 μm.

If the nutritional composition is in the form of a ready-to-use product, the osmolality of the nutritional composition may be between about 100 and about 1100 mOsm/kg water, more typically about 200 to about 700 mOsm/kg water.

In certain embodiments, the nutritional composition is hypoallergenic. In other embodiments, the nutritional composition is kosher and/or halal. In still further embodiments, the nutritional composition contains non-genetically modified ingredients. In an embodiment, the nutritional formulation is sucrose-free. The nutritional composition may also be lactose-free. In other embodiments, the nutritional composition does not contain any medium-chain triglyceride oil. In some embodiments, no carrageenan is present in the composition. In other embodiments, the nutritional composition is free of all gums.

The nutritional composition of the present disclosure is not limited to compositions comprising nutrients specifically listed herein. Any nutrients may be delivered as part of the composition for the purpose of meeting nutritional needs and/or in order to optimize the nutritional status in a subject.

Moreover, in some embodiments, the nutritional composition is nutritionally complete, containing suitable types and amounts of lipids, carbohydrates, proteins, vitamins and minerals to be a subject's sole source of nutrition. Indeed, the nutritional composition may optionally include any number of proteins, peptides, amino acids, fatty acids, probiotics and/or their metabolic by-products, prebiotics, carbohydrates and any other nutrient or other compound that may provide many nutritional and physiological benefits to a subject. Further, the nutritional composition of the present disclosure may comprise flavors, flavor enhancers, sweeteners, pigments, vitamins, minerals, therapeutic ingredients, functional food ingredients, food ingredients, processing ingredients or combinations thereof.

The nutritional composition of the present disclosure may be standardized to a specific caloric content, it may be provided as a ready-to-use product, or it may be provided in a concentrated form.

In some embodiments, the nutritional composition of the present disclosure is a growing-up milk. Growing-up milks are fortified milk-based beverages intended for children over 1 year of age (typically from 1-3 years of age, from 4-6 years of age or from 1-6 years of age). They are not medical foods and are not intended as a meal replacement or a supplement to address a particular nutritional deficiency. Instead, growing-up milks are designed with the intent to serve as a complement to a diverse diet to provide additional insurance that a child achieves continual, daily intake of all essential vitamins and minerals, macronutrients plus additional functional dietary components, such as non-essential nutrients that have purported health-promoting properties.

The exact composition of a nutritional composition according to the present disclosure can vary from market-to-market, depending on local regulations and dietary intake information of the population of interest. In some embodiments, nutritional compositions according to the disclosure consist of a milk protein source, such as whole or skim milk, plus added sugar and sweeteners to achieve desired sensory properties, and added vitamins and minerals. The fat composition is typically derived from the milk raw materials. Total protein can be targeted to match that of human milk, cow milk or a lower value. Total carbohydrate is usually targeted to provide as little added sugar, such as sucrose or fructose, as possible to achieve an acceptable taste. Typically, Vitamin A, calcium and Vitamin D are added at levels to match the nutrient contribution of regional cow milk. Otherwise, in some embodiments, vitamins and minerals can be added at levels that provide approximately 20% of the dietary reference intake (DRI) or 20% of the Daily Value (DV) per serving. Moreover, nutrient values can vary between markets depending on the identified nutritional needs of the intended population, raw material contributions and regional regulations.

One or more vitamins and/or minerals may also be added in to the nutritional composition in amounts sufficient to supply the daily nutritional requirements of a subject. It is to be understood by one of ordinary skill in the art that vitamin and mineral requirements will vary, for example, based on the age of the child. For instance, an infant may have different vitamin and mineral requirements than a child between the ages of one and thirteen years. Thus, the embodiments are not intended to limit the nutritional composition to a particular age group but, rather, to provide a range of acceptable vitamin and mineral components.

In embodiments providing a nutritional composition for a child, the composition may optionally include, but is not limited to, one or more of the following vitamins or derivations thereof: vitamin $B_1$ (thiamin, thiamin pyrophosphate, TPP, thiamin triphosphate, TTP, thiamin hydrochloride, thiamin mononitrate), vitamin $B_2$ (riboflavin, flavin mononucleotide, FMN, flavin adenine dinucleotide, FAD, lactoflavin, ovoflavin), vitamin $B_3$ (niacin, nicotinic acid, nicotinamide, niacinamide, nicotinamide adenine dinucleotide, NAD, nicotinic acid mononucleotide, NicMN, pyridine-3-carboxylic acid), vitamin $B_3$-precursor tryptophan, vitamin $B_6$ (pyridoxine, pyridoxal, pyridoxamine, pyridoxine hydrochloride), pantothenic acid (pantothenate, panthenol), folate (folic acid, folacin, pteroylglutamic acid), vitamin $B_{12}$ (cobalamin, methylcobalamin, deoxyadenosylcobalamin, cyanocobalamin, hydroxycobalamin, adenosylcobalamin), biotin, vitamin C (ascorbic acid), vitamin A (retinol, retinyl acetate, retinyl palmitate, retinyl esters with other long-chain fatty acids, retinal, retinoic acid, retinol esters), vitamin D (calciferol, cholecalciferol, vitamin $D_3$, 1,25,-dihydroxyvitamin D), vitamin E ($\alpha$-tocopherol, $\alpha$-tocopherol acetate, $\alpha$-tocopherol succinate, $\alpha$-tocopherol nicotinate, $\alpha$-tocopherol), vitamin K (vitamin $K_1$, phylloquinone, naphthoquinone, vitamin $K_2$, menaquinone-7, vitamin $K_3$, menaquinone-4, menadione, menaquinone-8, menaquinone-8H, menaquinone-9, menaquinone-9H, menaquinone-10, menaquinone-11, menaquinone-12, menaquinone-13), choline, inositol, $\beta$-carotene and any combinations thereof.

In embodiments providing a children's nutritional product, such as a growing-up milk, the composition may optionally include, but is not limited to, one or more of the following minerals or derivations thereof: boron, calcium, calcium acetate, calcium gluconate, calcium chloride, calcium lactate, calcium phosphate, calcium sulfate, chloride, chromium, chromium chloride, chromium picolonate, copper, copper sulfate, copper gluconate, cupric sulfate, fluoride, iron, carbonyl iron, ferric iron, ferrous fumarate, ferric orthophosphate, iron trituration, polysaccharide iron, iodide, iodine, magnesium, magnesium carbonate, magnesium hydroxide, magnesium oxide, magnesium stearate, magnesium sulfate, manganese, molybdenum, phosphorus, potassium, potassium phosphate, potassium iodide, potassium chloride, potassium acetate, selenium, sulfur, sodium, docusate sodium, sodium chloride, sodium selenate, sodium molybdate, zinc, zinc oxide, zinc sulfate and mixtures thereof. Non-limiting exemplary derivatives of mineral compounds include salts, alkaline salts, esters and chelates of any mineral compound.

The minerals can be added to growing-up milks or to other children's nutritional compositions in the form of salts such as calcium phosphate, calcium glycerol phosphate, sodium citrate, potassium chloride, potassium phosphate, magnesium phosphate, ferrous sulfate, zinc sulfate, cupric sulfate, manganese sulfate, and sodium selenite. Additional vitamins and minerals can be added as known within the art.

In an embodiment, the children's nutritional composition may contain between about 10 and about 50% of the maximum dietary recommendation for any given country, or between about 10 and about 50% of the average dietary recommendation for a group of countries, per serving, of vitamins A, C, and E, zinc, iron, iodine, selenium, and choline. In another embodiment, the children's nutritional composition may supply about 10-30% of the maximum dietary recommendation for any given country, or about 10-30% of the average dietary recommendation for a group of countries, per serving of B-vitamins. In yet another embodiment, the levels of vitamin D, calcium, magnesium, phosphorus, and potassium in the children's nutritional product may correspond with the average levels found in milk. In other embodiments, other nutrients in the children's nutritional composition may be present at about 20% of the maximum dietary recommendation for any given country, or about 20% of the average dietary recommendation for a group of countries, per serving.

The nutritional composition(s) of the present disclosure may optionally include one or more of the following flavoring agents, including, but not limited to, flavored extracts, volatile oils, cocoa or chocolate flavorings, peanut butter flavoring, cookie crumbs, vanilla or any commercially available flavoring. Examples of useful flavorings include, but are not limited to, pure anise extract, imitation banana extract, imitation cherry extract, chocolate extract, pure lemon extract, pure orange extract, pure peppermint extract, honey, imitation pineapple extract, imitation rum extract, imitation strawberry extract, grape and or grape seed extracts, apple extract, bilberry extract or vanilla extract; or volatile oils, such as balm oil, bay oil, bergamot oil, cedarwood oil, cherry oil, cinnamon oil, clove oil, or peppermint oil; peanut butter, chocolate flavoring, vanilla cookie crumb, butterscotch, toffee, and mixtures thereof. The amounts of flavoring agent can vary greatly depending upon the flavoring agent used. The type and amount of flavoring agent can be selected as is known in the art.

The nutritional compositions of the present disclosure may optionally include one or more emulsifiers that may be added for stability of the final product. Examples of suitable emulsifiers include, but are not limited to, lecithin (e.g., from egg or soy or any other plant and animal sources), alpha lactalbumin and/or mono- and di-glycerides, and mixtures thereof. Other emulsifiers are readily apparent to the skilled artisan and selection of suitable emulsifier(s) will depend, in part, upon the formulation and final product.

The nutritional compositions of the present disclosure may optionally include one or more preservatives that may also be added to extend product shelf life. Suitable preservatives include, but are not limited to, potassium sorbate, sodium sorbate, potassium benzoate, sodium benzoate, calcium disodium EDTA, and mixtures thereof.

The nutritional compositions of the present disclosure may optionally include one or more stabilizers. Suitable stabilizers for use in practicing the nutritional composition of the present disclosure include, but are not limited to, gum arabic, gum ghatti, gum karaya, gum tragacanth, agar, furcellaran, guar gum, gellan gum, locust bean gum, pectin, low methoxyl pectin, gelatin, microcrystalline cellulose, CMC (sodium carboxymethylcellulose), methylcellulose hydroxypropyl methyl cellulose, hydroxypropyl cellulose, DATEM (diacetyl tartaric acid esters of mono- and diglycerides), dextran, carrageenans, CITREM, and mixtures thereof.

The nutritional compositions described herein, in some embodiments, advantageously reduce the inflammatory response in a subject. Accordingly, the disclosure relates to methods of reducing a proinflammatory response in a subject by administering to a subject a nutritional composition containing the protein equivalent source described herein. For example, the present methods may reduce the production of proinflammatory cytokines in a subject. More particularly, the disclosure relates to methods of reducing IL-17 production by providing a target subject the nutritional composition containing the peptide component described herein.

In some embodiments, the method for reducing an inflammatory response in a subject comprises administering to a subject a nutritional composition comprising a carbohydrate source, a protein equivalent source and fat source, wherein the protein equivalent source includes a) a peptide component comprising SEQ ID NO 4, SEQ ID NO 13, SEQ ID NO 17, SEQ ID NO 21, SEQ ID NO 24, SEQ ID NO 30, SEQ ID NO 31, SEQ ID NO 32, SEQ ID NO 51, SEQ ID NO 57, SEQ ID NO 60, and SEQ ID NO 63, and b) an intact protein, a hydrolyzed protein, or a combination thereof. In some embodiments, the peptide component may comprise additional peptides disclosed in Table 1. For example, the composition may include at least 10 additional peptides disclosed in Table 1. In some embodiments, 20% to 80% of the protein equivalent source comprises the peptide component, and 20% to 80% of the protein equivalent source comprises an intact protein, a partially hydrolyzed protein, and combinations thereof.

In another embodiment, the method comprises administering to a subject a nutritional composition, wherein 20% to 80% of the protein equivalent source includes a peptide component comprising at least 3 peptides selected from the group consisting of SEQ ID NO 4, SEQ ID NO 13, SEQ ID NO 17, SEQ ID NO 21, SEQ ID NO 24, SEQ ID NO 30, SEQ ID NO 31, SEQ ID NO 32, SEQ ID NO 51, SEQ ID NO 57, SEQ ID NO 60, and SEQ ID NO 63, and at least 5 additional peptides selected from Table 1; and wherein 20% to 80% of the protein equivalent source comprises an intact protein, a partially hydrolyzed protein, or combinations thereof.

In yet other embodiments, the method for reducing the inflammatory response includes providing a nutritional composition comprising a peptide component from Table 1, wherein the peptide component is derived from a casein hydrolysate having a molar mass distribution of greater than 500 Daltons. In some embodiments, the molar mass distribution of the casein hydrolysate is in a range of 500 to 2000 Daltons. In other embodiments, the method for reducing inflammatory response includes providing a nutritional composition comprising the peptide component described herein, wherein the peptide component is derived from a casein hydrolysate that does not include peptides having a molar mass distribution of less than 200 Daltons.

In some embodiments the target subject may be a pediatric subject. Further, in one embodiment, the nutritional composition provided to the pediatric subject may be an infant formula. The peptide component identified herein and added to the infant formula may be selected from a specific source and concentrations thereof may be adjusted to maximize health benefits. In another embodiment of this method, the nutritional composition comprising the peptide component disclosed herein is a growing up milk.

In embodiments when the nutritional composition is an infant formula, the composition may advantageously reduce a proinflammatory response in the infant, and thereby reduce the incidence of inflammatory disease. Moreover, the reduction in inflammatory disease may last throughout childhood and into adulthood. Similarly, when the nutritional composition is a growing-up milk, a child who ingests the growing-up milk may experience a reduction in the incidence of inflammatory disease in adulthood, as well as during childhood.

FORMULATION EXAMPLES

Table 3 provides an example embodiment of a peptide component including 8 peptides from Table.

TABLE 3

| Example peptide component Example of Selected Peptides for Peptide Component |
| --- |
| SEQ ID NO 5 |
| SEQ ID NO 24 |
| SEQ ID NO 33 |
| SEQ ID NO 56 |
| SEQ ID NO 64 |
| SEQ ID NO 13 |
| SEQ ID NO 24 |
| SEQ ID NO 60 |

Table 4 provides an example embodiment of a peptide component including certain peptides from Table 1.

TABLE 4

Example peptide component
Example of Selected Peptides
for Peptide Component

SEQ ID NO 13
SEQ ID NO 24
SEQ ID NO 60
SEQ ID NO 5
SEQ ID NO 11
SEQ ID NO 22
SEQ ID NO 25
SEQ ID NO 33
SEQ ID NO 45
SEQ ID NO 46
SEQ ID NO 47
SEQ ID NO 48
SEQ ID NO 52
SEQ ID NO 34
SEQ ID NO 36
SEQ ID NO 61
SEQ ID NO 62
SEQ ID NO 64

Table 5 provides an example embodiment of a nutritional composition according to the present disclosure and describes the amount of each ingredient to be included per 100 kcal serving.

TABLE 5

Nutrition profile of an example nutritional composition

| Nutrient | per 100 kcal | |
|---|---|---|
| | Minimum | Maximum |
| Protein Equivalent Source (g) | 1.0 | 7.0 |
| Carbohydrates (g) | 6 | 22 |
| Fat (g) | 1.3 | 7.2 |
| Prebiotic (g) | 0.3 | 1.2 |
| DHA (g) | 4 | 22 |
| Beta glucan (mg) | 2.9 | 17 |
| Probiotics (cfu) | 0.5 | 5.0 |
| Vitamin A (IU) | $9.60 \times 10^5$ | $3.80 \times 10^8$ |
| Vitamin D (IU) | 134 | 921 |
| Vitamin E (IU) | 22 | 126 |
| Vitamin K (mcg) | 0.8 | 5.4 |
| Thiamin (mcg) | 2.9 | 18 |
| Riboflavin (mcg) | 63 | 328 |
| Vitamin B6 (mcg) | 68 | 420 |
| Vitamin B12 (mcg) | 52 | 397 |
| Niacin (mcg) | 0.2 | 0.9 |
| Folic acid (mcg) | 690 | 5881 |
| Panthothenic acid (mcg) | 8 | 66 |
| Biotin (mcg) | 232 | 1211 |
| Vitamin C (mg) | 1.4 | 5.5 |
| Choline (mg) | 4.9 | 24 |
| Calcium (mg) | 4.9 | 43 |
| Phosphorus (mg) | 68 | 297 |
| Magnesium (mg) | 54 | 210 |
| Sodium (mg) | 4.9 | 34 |
| Potassium (mg) | 24 | 88 |
| Chloride (mg) | 82 | 346 |
| Iodine (mcg) | 53 | 237 |
| Iron (mg) | 8.9 | 79 |
| Zinc (mg) | 0.7 | 2.8 |
| Manganese (mcg) | 0.7 | 2.4 |
| Copper (mcg) | 7.2 | 41 |

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references.

Although embodiments of the disclosure have been described using specific terms, devices, and methods, such description is for illustrative purposes only. The words used are words of description rather than of limitation. It is to be understood that changes and variations may be made by those of ordinary skill in the art without departing from the spirit or the scope of the present disclosure, which is set forth in the following claims. In addition, it should be understood that aspects of the various embodiments may be interchanged in whole or in part. For example, while methods for the production of a commercially sterile liquid nutritional supplement made according to those methods have been exemplified, other uses are contemplated. Therefore, the spirit and scope of the appended claims should not be limited to the description of the versions contained therein.

What is claimed is:

1. A nutritional composition, comprising:
   (i) a carbohydrate source;
   (ii) a fat source; and
   (iii) a protein equivalent source;
   wherein
   a) 20% to 80% of the protein equivalent source includes a peptide component comprising the following peptides: SEQ ID NO 4, SEQ ID NO 13, SEQ ID NO 17, SEQ ID NO 21, SEQ ID NO 24, SEQ ID NO 30, SEQ ID NO 32 SEQ ID NO 51, SEQ ID NO 57, SEQ ID NO 60, and SEQ ID NO 63; further wherein the peptide component comprises at least 3 additional individual peptides selected from Table 1; and
   b) 20% to 80% of the protein equivalent source comprises an intact protein and a partially hydrolyzed protein.

2. The nutritional composition of claim 1, comprising at least 10 additional peptides selected from Table 1.

3. The nutritional composition of claim 1, wherein the protein equivalent source comprises casein hydrolysate having a molar mass distribution of greater than 500 Daltons.

4. The nutritional composition of claim 1, wherein the protein equivalent source comprises partially hydrolyzed protein having a degree of hydrolysis of less than 40%.

5. The nutritional composition of claim 1, further comprising a prebiotic.

6. The nutritional composition of claim 1, further comprising a culture supernatant from a late-exponential growth phase of a probiotic batch-cultivation process.

7. The nutritional composition of claim 1 wherein the peptide component is present in an amount of from about 0.2 g/100 kcals to about 5.6 g/100 kcals.

8. The nutritional composition of claim 1, further comprising β-glucan.

9. The nutritional composition of claim 1, further comprising a probiotic.

10. The nutritional composition of claim 1, further comprising at least one long-chain polyunsaturated fatty acid, wherein the at least one long-chain polyunsaturated fatty acid is selected from the group consisting of docosahexaenoic acid and arachidonic acid.

11. A nutritional composition comprising per 100 kcals:
   (i) from about 5 g to about 25 g of a carbohydrate source;
   (ii) from about 1.3 g to about 7.2 g of a fat source; and
   (iii) from about 1 g to about 7 g of a protein equivalent source;
wherein
   a) 20% to 80% of the protein equivalent source comprises a peptide component comprising the following peptides: SEQ ID NO 4, SEQ ID NO 13, SEQ ID NO 17, SEQ ID NO 21, SEQ ID NO 24, SEQ ID NO 30, SEQ ID NO 32 SEQ ID NO 51, SEQ ID NO 57, SEQ ID NO 60, and SEQ ID NO 63; wherein the peptide component further comprises at least 3 additional individual peptides selected from Table 1; and
   b) at least 20% of the protein equivalent source comprises a casein hydrolysate having a molar mass distribution of greater than 500 Daltons.

12. The nutritional composition of claim 11, wherein the peptide component further comprises at least 10 additional individual peptides selected from the group consisting of SEQ ID NO 1, SEQ ID NO 2, SEQ ID NO 3, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 14, SEQ ID NO 15, SEQ ID NO 16, SEQ ID NO 18, SEQ ID NO 19, SEQ ID NO 20, SEQ ID NO 22, SEQ ID NO 23, SEQ ID NO 25, SEQ ID NO 26, SEQ ID NO 27, SEQ ID NO 28, SEQ ID NO 29, SEQ ID NO 33, SEQ ID NO 34, SEQ ID NO 35, SEQ ID NO 36, SEQ ID NO 37, SEQ ID NO 38, SEQ ID NO 39, SEQ ID NO 40, SEQ ID NO 41, SEQ ID NO 42, SEQ ID NO 43, SEQ ID NO 44, SEQ ID NO 45, SEQ ID NO 46, SEQ ID NO 47, SEQ ID NO 48, SEQ ID NO 49, SEQ ID NO 50, SEQ ID NO 52, SEQ ID NO 53, SEQ ID NO 54, SEQ ID NO 55, SEQ ID NO 56, SEQ ID NO 58, SEQ ID NO 59, SEQ ID NO 61, SEQ ID NO 62, and SEQ ID NO 64.

13. The nutritional composition of claim 11, further comprising at least one long-chain polyunsaturated fatty acid.

14. The nutritional composition of claim 11, further comprising at least one probiotic.

15. The nutritional composition of claim 11, further comprising at least one prebiotic.

16. The nutritional composition of claim 11, further comprising β-glucan.

* * * * *